US008747739B2

United States Patent
Parker et al.

(10) Patent No.: US 8,747,739 B2
(45) Date of Patent: Jun. 10, 2014

(54) MAINTAINING DISINFECTION OF MEDICAL EQUIPMENT

(75) Inventors: George Christopher Parker, Westcliff-on-Sea (GB); Barry Luke, Canvey Island (GB)

(73) Assignee: Medicart International Limited (GB)

( * ) Notice: Subject to any disclaimer, the term of this patent is extended or adjusted under 35 U.S.C. 154(b) by 672 days.

(21) Appl. No.: 12/083,846

(22) PCT Filed: Oct. 27, 2006

(86) PCT No.: PCT/GB2006/050356
§ 371 (c)(1),
(2), (4) Date: Apr. 18, 2008

(87) PCT Pub. No.: WO2007/049076
PCT Pub. Date: May 3, 2007

(65) Prior Publication Data
US 2009/0123333 A1    May 14, 2009

(30) Foreign Application Priority Data
Oct. 29, 2005 (GB) .................................. 0522102.3

(51) Int. Cl.
A61L 2/20    (2006.01)
(52) U.S. Cl.
USPC ............. 422/33; 422/294; 422/298; 422/300; 206/363; 206/438
(58) Field of Classification Search
USPC ............. 422/28, 33, 292, 294, 295, 298, 300; 206/363, 370, 438, 439
See application file for complete search history.

(56) References Cited

U.S. PATENT DOCUMENTS

| 5,310,524 | A  |   | 5/1994  | Campbell |
| 5,378,428 | A  | * | 1/1995  | Inoue et al. ........................ 422/9 |
| 5,534,221 | A  | * | 7/1996  | Hillebrenner et al. ........... 422/33 |
| 6,164,738 | A  | * | 12/2000 | Dane et al. ...................... 312/311 |
| 6,312,645 | B1 |   | 11/2001 | Lin et al. |
| 6,749,063 | B2 | * | 6/2004  | Parker ........................... 206/363 |
| 2003/0138347 | A1 | * | 7/2003 | Lin .................................. 422/28 |
| 2004/0188304 | A1 | * | 9/2004 | Bonnette et al. ............ 206/459.1 |
| 2005/0147527 | A1 | * | 7/2005 | Brown et al. .................... 422/33 |
| 2005/0268573 | A1 | * | 12/2005 | Yan ................................. 53/425 |

FOREIGN PATENT DOCUMENTS

| GB | 2381521 | 5/2003 |
| WO | WO/2005/073091 | 8/2005 |
| WO | WO/2005/120395 | 12/2005 |

\* cited by examiner

Primary Examiner — Timothy Cleveland
(74) Attorney, Agent, or Firm — Renner Kenner Greive Bobak Taylor & Weber

(57) ABSTRACT

A method is provided for maintaining the disinfection of medical equipment, in particular medical endoscopes (10), following processing. The method comprises placing the disinfected equipment (10) in a sealed chamber (12), and subsequently reducing the pressure within the sealed chamber (12) to cause evaporation of residual moisture. Gas scavenger sachets (21) are also provided within the sealed chamber (12) to remove atmospheric oxygen, thus causing a further reduction in the chamber pressure. The method may optionally include a further step of charging the sealed chamber (12) with a disinfectant gas or vapor. The processed medical equipment (10) is then maintained at the desired level of disinfection within the controlled biostatic environment in the sealed chamber (12).

12 Claims, 3 Drawing Sheets

MAINTAINING DISINFECTION OF MEDICAL EQUIPMENT

This invention relates to a method for maintaining the disinfection of medical equipment immediately following the equipment being disinfected, and to apparatus for use in such a method.

The term "disinfection" is used herein in preference to the term "sterility" since the latter implies the complete absence of pathogenic organisms, which in practice is rarely, if ever, achievable. It is to be appreciated however that the ultimate aim of disinfecting medical equipment is indeed to get as close to absolute sterility as is practicable.

The present invention has been developed in connection with the processing and storage of flexible medical endoscopes, and therefore will be described herein with particular emphasis on this application. It is envisaged however, that the method of the present invention may be applied to the processing and storage of substantially all types of medical, surgical, dental and veterinary equipment, apparatus, and instruments.

After use in a surgical procedure, articles of medical equipment such as endoscopes, are usually subjected to a rigorous cleaning and disinfecting procedure, before being stored in a disinfected environment. An example of a suitable storage environment is disclosed in the applicant's own publication no. GB 2,381,521 A, which describes a deep-dished tray having a liner with a protective cover for isolating an endoscope (or other medical equipment) stored therein, from the surrounding atmosphere.

When stored in such a way, the degree of disinfection of the endoscope can be maintained at an acceptable level for a finite period—usually about 3 hours. This is due to the multiplication of residual pathogens which may remain on the endoscope after disinfection, or which may be present in the atmosphere. If the endoscope is not used in a further surgical procedure within this time, then further cleaning and disinfection ("processing") will be necessary prior to its next use. Frequent and repeated processing is undesirable, since it reduces the availability of the endoscope for surgical procedures, whilst increasing the operating costs, due to the need for cleaning and disinfectant materials and the operation of cleaning equipment. Furthermore, repeated processing reduces the lifetime of the endoscope due to wear and tear.

Previous attempts to extend the viable storage time of endoscopes between surgical procedures, include the use of storage cabinets, which may accommodate several endoscopes. Air is continuously circulated through the cabinets, usually passed through filters and silica gel, and the stored endoscopes may also be irradiated with ultra-violet light. A disadvantage of such a system is that storing several endoscopes together increases the risk of cross-contamination. Additionally, the disinfected environment will be disturbed whenever the cabinet is opened to insert or remove an endoscope, so that all endoscopes stored within the cabinet are exposed to the ambient—and whatever biological contaminants are contained therein—every time a single endoscope is inserted or removed. Furthermore, the use of UV light can lead to degradation of rubber and plastics components of the endoscopes.

The present invention seeks to address these issues by providing a method by which the viable inter-procedural disinfected storage time of endoscopes, and other medical equipment, may be extended from the current UK standard of 3 hours, to perhaps more than 500 hours. The method of the present invention is cost effective and causes no deterioration in the condition of the endoscope. The method of the present invention may be used independently in conjunction with any suitable apparatus, however it is believed that it will be particularly effective when used in combination with the apparatus described in the applicant's publication No. GB 2,381,521 A.

According to the present invention there is provided a method for maintaining the disinfection of medical equipment following processing thereof, comprising placing the disinfected equipment in a sealed chamber, and subsequently performing the following steps:

(A) reducing the pressure within the sealed chamber to cause evaporation of residual moisture;

(B) removing atmospheric oxygen therefrom by means of a gas scavenger;

and optionally:

(C) charging the sealed chamber with a disinfectant gas or vapour;

and subsequently maintaining a biostatic environment within the sealed chamber.

The term "sealed" as used herein with reference to the chamber in which the processed medical equipment is placed, should be construed as meaning that the chamber is isolated from the ambient by the provision of a substantially gas-tight seal. However, since certain aspects of the method of the present invention concern the delivery and removal of gases and vapours to and from the chamber, it should be appreciated that total hermetic sealing of the chamber is not intended.

Steps (A) and (B) of the method of the present invention may be performed either sequentially, or simultaneously, and the method may be performed either with or without step (C). Preferably however, all of steps (A), (B) and (C) are performed.

The reduction of pressure in step (A) is preferably achieved by a manual, mechanical or electrical suction device. The reduced pressure provides a benefit to the system in that it facilitates the vaporisation of any residual moisture which may be present on the medical equipment or in the internal channels thereof. This water vapour, together with atmospheric water vapour, may then be removed from the sealed chamber by use of a standard desiccant such as silica gel.

By removing water vapour from the sealed chamber, it is possible to control the population of anaerobic micro-organisms, since water acts as a solvent for many nutrients required by such micro-organisms.

By removing oxygen from the sealed chamber in step (B) using oxygen scavengers, aerobic micro-organisms present within the environment will be deprived of an essential ingredient required for their survival, and their ability to multiply will be inhibited. In theory, if all oxygen were removed from the environment, then multiplication of aerobic pathogens would decrease to zero, and the population would remain static.

The removal of atmospheric oxygen from the sealed environment results in a further decrease in the chamber's pressure, so long as the volume of the chamber remains constant, and it is therefore preferable that the chamber has a rigid construction. The further reduction in pressure is due to the elimination of the partial pressure exerted by the removed gas—thus if all atmospheric oxygen were removed from the sealed chamber, then the total pressure would decrease by approximately 20%.

A further advantage of the method of the present invention, is that the absence of oxygen and moisture in the chamber inhibits corrosion of the medical equipment, thus prolonging its usable lifetime.

Preferably, other gases may also be removed from the sealed chamber in step (B) by means of appropriate gas scavengers or "getters". In particular, gases such as carbon dioxide, hydrogen sulphide, sulphur dioxide, hydrogen chloride and ammonia, which are produced by micro-organisms, may be removed. These gases are produced by certain species of micro-organism, and subsequently act as nutrients for other species. Their removal from the sealed chamber serves to break the microbiological food chain, thus leading to a decrease in the pathogen population. Additionally, many of these gases are corrosive, and their removal thus prolongs the life of the stored medical equipment.

Suitable materials for use as oxygen scavengers include finely-divided iron powders, such as those sold under the trademark ATCO. Activated carbon pads, sometimes described as activated charcoal, may be used to "mop up" the biologically produced gases such as hydrogen sulphide.

Due to the reduced pressure within the sealed chamber, the disinfectant gas or vapour introduced in step (C) permeates through the internal channels etc. of the processed medical equipment. A sterile gas such as dry nitrogen gas may be used. However, it is generally preferred that the principal disinfectant agent in step (C) is vapour phase hydrogen peroxide (VPHP).

The hydrogen peroxide vapour may be introduced into the sealed chamber from a storage vessel via a metering system, with the input of VPHP being monitored and controlled by a micro-processor control unit in communication with said metering system.

Alternatively, the hydrogen peroxide vapour may be generated in situ by a VPHP generator, in communication with the sealed chamber. The generator is preferably adapted to produce droplets or an atomised spray of hydrogen peroxide vapour from an aqueous solution of at least 35% hydrogen peroxide, by weight.

Step (C) is optionally followed by an additional step (D), in which the pressure within the sealed chamber is reduced again to enable removal of the hydrogen peroxide vapour. The environment within the sealed chamber is then maintained in a biostatic condition by maintaining the reduced pressure and/or re-introducing a charge of dry sterile nitrogen gas.

The maintenance of the reduced pressure within the chamber during storage subsequent to steps (A), (B), (C) and (D), if present, is preferably achieved by maintaining communication between the sealed chamber and a mechanical or electrical suction device. In the event of a power failure during storage, the reduced pressure will be at least partially retained by the action of the gas scavengers, thus ensuring that the efficacy of the system is not compromised.

The sealed chamber itself is preferably provided with an oxygen level indicator, to provide a visual indication—such as a colour change—to inform a user as to the condition of the environment within the chamber i.e. whether the integrity of the sealed chamber has been compromised. Similarly, indicators could be used to show the moisture level, and levels of other gases desired to be controlled.

As stated above, it is believed that the method of the present invention particularly lends itself to use in conjunction with the apparatus described in the applicant's publication no. GB 2,381,521 A.

Therefore, in a preferred embodiment of the present invention, the sealed chamber comprises a re-usable tray having a downwardly-dished, inner compartment defined by a generally planar base, and surrounding walls upstanding therefrom, said tray being further provided with a single-use, disposable tray-liner formed of a flexibly deformable, sheet material such that in use the tray-liner is able to conform itself substantially to the contours of the underlying tray, and a protective cover formed of substantially inflexible material which in use can be detachably secured across the top of the inner compartment, thereby to provide a substantially gas tight seal.

The provision of a disposable liner in the tray enables a high level of cleanliness to be maintained. The liner is supplied in a sterile or near-sterile condition, and is discarded and replaced with a like liner after each use, thus removing the need for the tray to be disinfected between each use.

Clearly, it will be necessary to ensure that a gas-tight seal is provided between the protective cover and the tray, to create a sealed environment within the lined tray compartment, and that the cover is relatively inflexible so as to ensure that it does not sag into the tray as a result of the pressure loss. To achieve this, the protective cover preferably is, or further comprises, a rigid lid having tapered edges adapted to engage with complementary tapered edges provided on the walls of the tray.

The gas scavengers and the desiccant may conveniently be present in sachets placed within the liner. Where additional scavengers for gases other than oxygen are also employed, these may either be provided separately, or alternatively may be combined in a single unit with the oxygen scavenger sachet. It is envisaged that the scavengers will be supplied in a vacuum-sealed sachet, which could be activated by the removal of a tear-off strip to expose the scavengers to the environment within the chamber.

In a further variation of the method of the present invention, the entire assembly of the lined tray containing the processed medical equipment and activated scavenger sachets, is placed inside an oxygen-impermeable pouch, which is then sealed by means of a zip or other gas-tight sealing method to create a sealed environment.

It is envisaged that each of the inflexible protective cover and the oxygen-impermeable pouch may be used independently of the other, or alternatively the two may be used in combination. Indeed the tray and the oxygen-impermeable pouch may be used either independently of the other, or in combination. Where the pouch is used in the absence of the tray, the pouch itself forms the sealed chamber for the medical equipment.

The oxygen-impermeable pouch is preferably equipped with a valve adapted for connection to a mechanical or electrical suction device capable of removing some or substantially all of the air from within said pouch in step (A). A like valve is preferably also incorporated into the tray—and may be located either in a wall of the tray, or incorporated into the protective cover. Where both the tray and the pouch are used, the respective valves are arranged so as to enable communication therebetween.

The valve in the pouch and/or the tray may be further adapted for connection to a vessel or generator for the disinfectant gas or vapour, for the performance of step (C). Alternatively, separate ports in the tray and/or the pouch may be provided to enable the ingress of the disinfectant gas or vapour. To ensure that the volume of the pouch remains generally constant during the pressure reducing steps (A) and (B) and the gas charging step (C), the pouch may desirably be formed with a substantially inflexible construction.

In one embodiment of the method of the present invention, the valve is adapted for connection to a disinfection maintenance station comprising both a manual, electrical or mechanical suction device for the performance of step (A) and a vessel or generator for the disinfectant gas or vapour for the performance of step (C), combined within the same unit.

In a further variation of the present invention, multiple sealed chambers are provided within a rack or cabinet, to enable the disinfection of a plurality of articles of medical equipment to be maintained simultaneously, and independently of one another. This ensures that removal of a selected article of medical equipment from its sealed chamber does not compromise the disinfected condition of other articles of medical equipment also housed in like chambers within the rack or cabinet.

Preferably, the rack or cabinet comprises a plurality of disinfection maintenance stations, each comprising a port adapted to engage with the valve of the tray and/or the pouch, said port enabling connection of the sealed chamber to a mechanical, electrical or manual suction device for the performance of step (A). Most preferably, said port further enables connection of the sealed chamber to a vessel or generator for the disinfectant gas or vapour, for the performance of step (C).

The apparatus as hereinbefore described, for use in the method of the present invention, constitutes a further aspect of the present invention.

In order that the present invention may be more clearly understood, a preferred embodiment thereof will now be described in detail, though only by way of example, with reference to the accompanying drawings, in which:

FIGS. 1 to 6 together form a sequence illustrating a preferred embodiment of the method of the present invention, and the apparatus for use in such a method.

Figure 1:
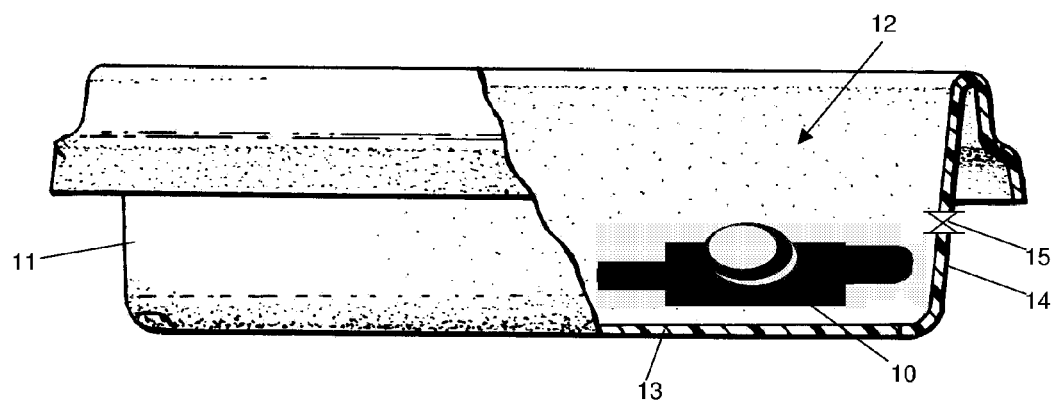
FIG. 1 is a partly cut-away side view showing a processed medical endoscope, placed in a lined tray ready to be treated according to the method of the present invention.

Referring first to FIG. 1, there is shown a medical endoscope, generally indicated 10, which is in a disinfected or "processed" state, having been subjected to rigorous cleaning and disinfecting, following use in a surgical procedure. On emerging from processing, the disinfected endoscope 10 is placed into a re-usable rigid tray 11 having a downwardly-dished, inner compartment, generally indicated 12, defined by a generally planar base 13, and surrounding walls 14 upstanding therefrom. One wall 14 of the tray 11 has a valve 15 formed therein, for connection to a disinfection maintenance station, as will be discussed in more detail below with reference to FIGS. 4 and 5.

Figure 2:
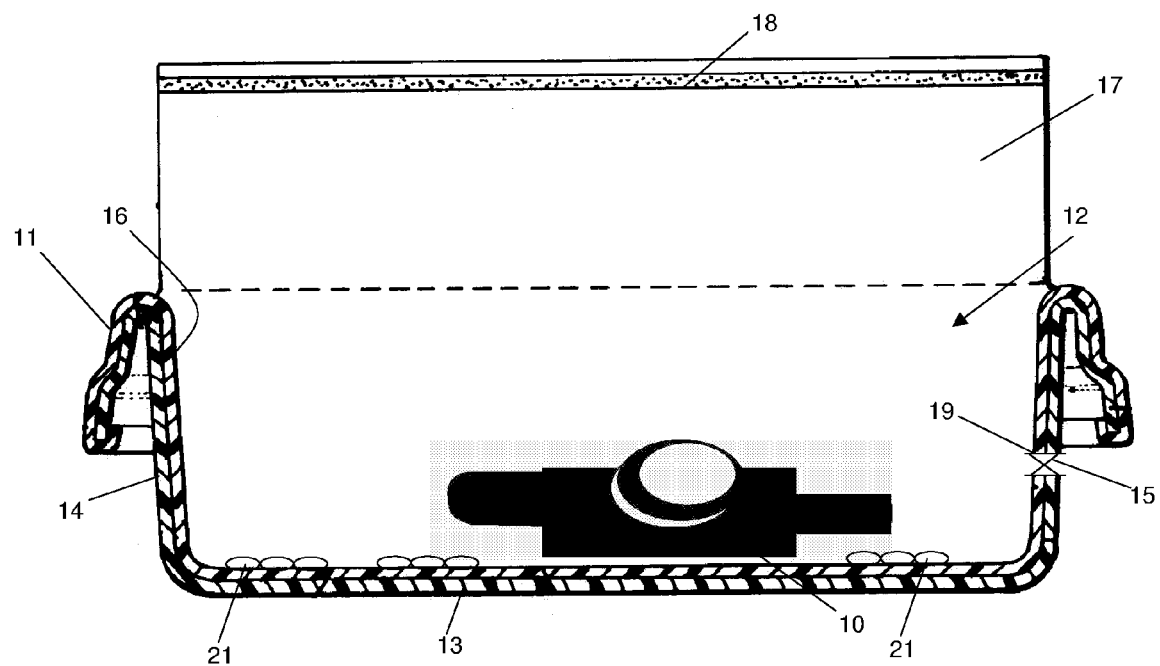
FIG. 2 is a cross-sectional view of the tray of FIG. 1, showing the liner in more detail, including the provision of gas scavenger sachets.

As is best seen in FIG. 2, the tray 11 is provided with a single-use, disposable liner 16, formed of a flexibly deformable, sheet material which enables the liner 16 to conform itself substantially to the contours of the base 13 and walls 14 of the underlying tray 11. The liner 16 has a flap 17 which is adapted to be extended across the inner compartment 12 of the tray 11, and secured to an opposed wall 14 of the tray 11 by means of an adhesive strip 18. Alternatively, the liner 16 may be provided with a separate cover (not shown) having an elasticated rim. The liner 16 is also provided with an aperture 19 to enable the valve 15 to communicate with the inner compartment 12 within the liner 16.

Scavenger sachets 21 are located within the liner 16, either being placed therein along with the processed endoscope 10, or being integrally formed within the liner 16. The sachets 21 contain oxygen scavengers, further scavengers or "getters" for other gases, and silica gel desiccant. The scavenger sachets 21 are activated by removing a tear-off strip (not shown) to expose the scavengers to the atmosphere within the inner compartment 12 of the tray 11, before the compartment 12 is sealed by closing the flap 17.

Figure 3:
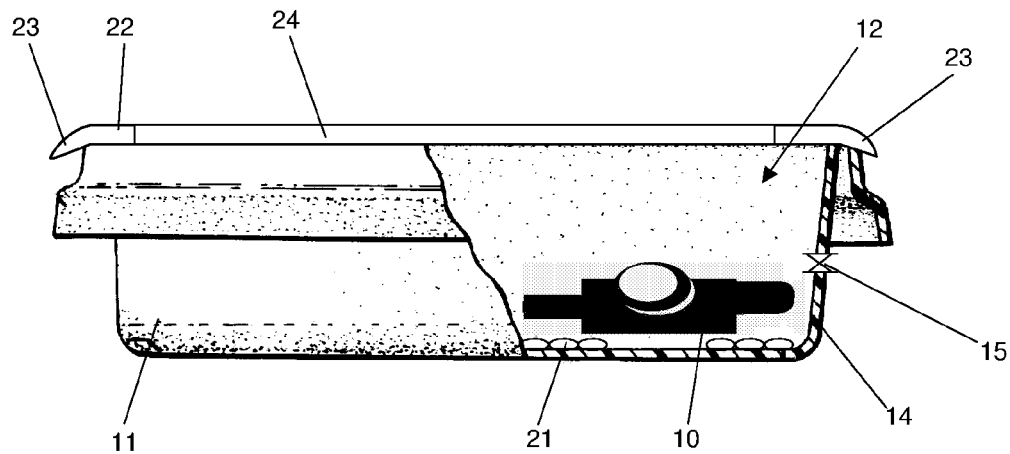
FIG. 3 is a partly cut-away side view showing the tray of FIGS. 1 and 2 sealed for the performance of the oxygen scavenging step of the method of the present invention.

Referring now to FIG. 3, the endoscope 10 and scavenger sachets 21 are now isolated from the ambient, within the inner compartment 12 of the tray 11. In order to ensure a substantially air-tight seal, such that the inner compartment 12 forms a sealed chamber as hereinbefore described in the method of the present invention, a rigid protective cover 22 is then placed over the tray 11. The cover 22 has tapered edges 23 to provide a substantially air-tight seal by co-operating with complementary tapers (not shown) provided on the upper edges of the walls 14 of the tray 11. The cover 22 is further provided with a viewing window 24 in order that the condition of the endoscope 10 within the compartment 12 may be monitored. The viewing window 24 may be provided with an oxygen level indicator (not shown), to provide a visual indication of the condition of the compartment 12, for example by means of a colour change.

The scavengers 21 within the sealed compartment 12 act to decrease the oxygen levels within the compartment, thus inhibiting the multiplication of aerobic micro-organisms, and leading to a decrease in their population. The oxygen decrease also leads to reduction in the gas pressure within the sealed compartment 12, as a result of the air-tight seal provided by the liner flap 17 and the rigid cover 22. The reduced pressure encourages residual water present in the compartment 12 to evaporate, whereupon it is removed by the silica gel desiccant within the scavenger sachets 21, along with water vapour naturally present in the air within the compartment 12. The removal of water prevents access to nutrients dissolved therein, thus inhibiting the multiplication of both aerobic and anaerobic micro-organisms.

Figure 4:
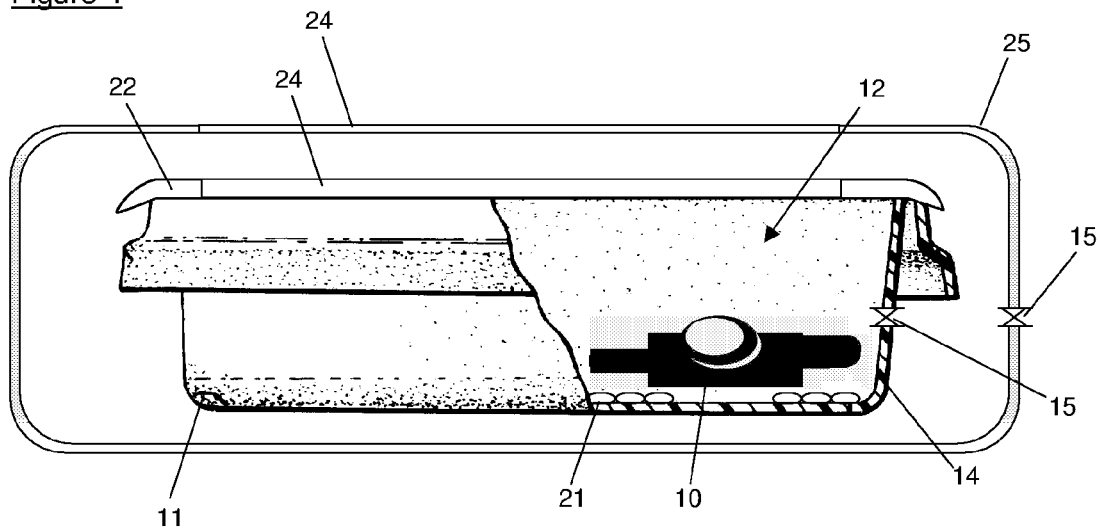
FIG. 4 is a partly cut-away side view showing the tray of FIGS. 1 to 3, further sealed in an oxygen-impermeable pouch for the performance of the oxygen scavenging step of the method of the present invention.

As shown in FIG. 4, the sealing of the compartment 12 from the ambient may be further enhanced by placing the entire assembly of endoscope 10, tray 11, liner 16, sachets 21 and cover 22 into an oxygen-impermeable, substantially inflexible pouch 25. The pouch 25 is provided with a valve 15 and a viewing window 24, which are arranged so as to be aligned respectively with the valve 15 in the tray 11 and the viewing window 24 in the tray cover 22. The valve 15 in the tray 11 and/or the pouch 25 may be connected to a suction device (not shown) to evacuate air from within the pouch 25, thus causing a further reduction in the gas pressure within the compartment 12, as described above. Although described here as separate method steps, the pressure reducing step and the oxygen scavenging step will in practice be carried out virtually simultaneously.

In preferred embodiments of the method of the present invention, the valves 15 of the tray 11 and the pouch 25 are connected to a disinfection maintenance station, as will now be described in more detail with reference to FIGS. 5 and 6. The processed endoscope 11 within the sealed compartment 12 is treated by performing: an oxygen scavenging step, as described above with reference to FIGS. 2 to 3; a step of reducing the pressure within the sealed compartment 12 by connecting the valve 15 of the tray 11 and/or the pouch 25 to a mechanical, electrical or manual suction device (not shown), as described above with reference to FIG. 4; and a step of charging the sealed compartment 12 with a disinfectant gas or vapour such as dry nitrogen gas, or vapour phase hydrogen peroxide, by introducing said gas or vapour through the valve 15 of the tray 11 and/or the pouch 25.

As noted above, although described here as separate method steps, the pressure reducing step and the oxygen scavenging step will in practice be carried out virtually simultaneously.

Figure 5:
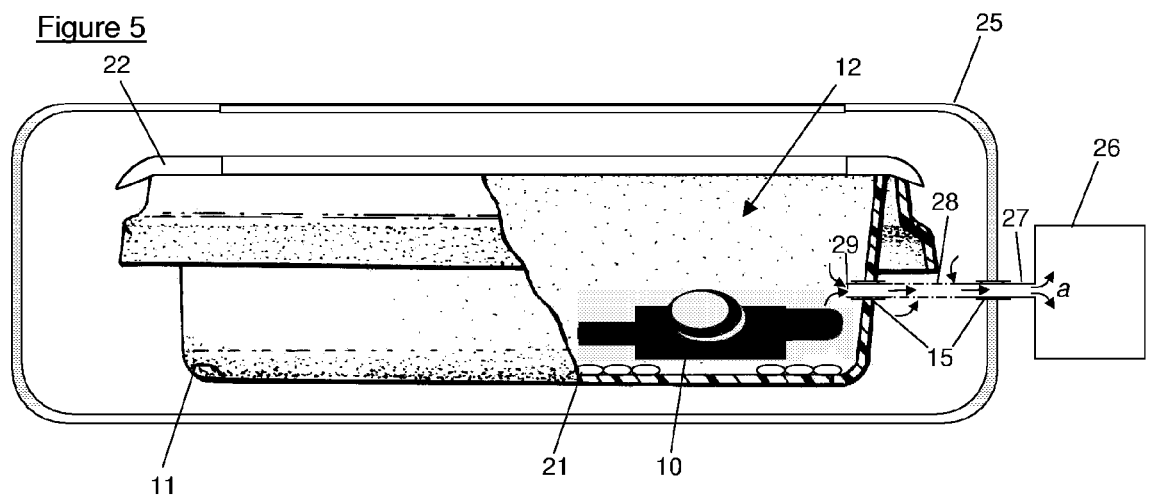
FIG. 5 is a partly cut-away side view showing the tray and pouch assembly of FIG. 4 docked with a disinfection maintenance station for the performance of the pressure reducing step of the method of the present invention.
Figure 6:
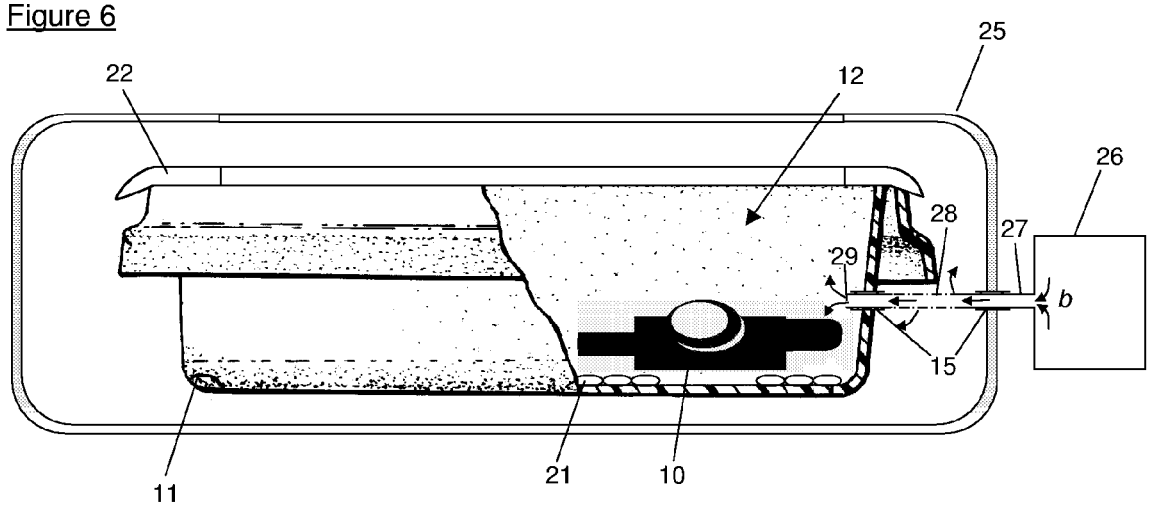
FIG. 6 is a partly cut-away side view showing the tray and pouch assembly of FIG. 4 docked with a disinfection maintenance station for the performance of the gas charging step of the method of the present invention.

To facilitate the performance of the method of the present invention, the combined tray 11 and pouch 25 assembly is adapted to be docked with a disinfection maintenance station 26, which is schematically represented in FIGS. 5 and 6. The disinfection maintenance station 26 comprises both a mechanical, electrical or manual suction device for evacuating the sealed compartment 12 in the pressure reducing step, as indicated by arrows a in FIG. 5; and a vessel or generator for charging the compartment 12 with the disinfectant gas or vapour in the gas charging step, as indicated by arrows b in FIG. 6.

The docking of the respective valves 15 of the tray 11 and/or pouch 25 with the disinfection maintenance station 26 can be achieved in a variety of ways, depending on the particular embodiment of the method of the present invention being performed, and the precise configuration of the apparatus being utilised in that method. In the preferred embodiment illustrated in FIGS. 5 and 6, the respective valves 15 of the tray 11 and the pouch 25 are both docked with a single port 27 of the disinfection maintenance station 26, said port 27 being used for both the removal a of air from the sealed compartment 12, and the charging b of the compartment 12 with the disinfectant gas or vapour. The port 27 may be provided with apertures 28 along its length so as to permit the ingress a and egress b of gas and/or vapour into and out of the pouch 25 as well as into and out of the sealed compartment 12 at its end 29.

A typical sequence for the performance of the preferred embodiment of the method of the present invention, will now be described, with reference to FIGS. 5 and 6:

After docking the tray 11 and pouch 25 assembly with the disinfection maintenance station 26, the sealed compartment 12 is connected to a mechanical suction device within the station 26 so as to evacuate air therefrom, as indicated by arrows a in FIG. 5. Following this, the sealed compartment 12 is connected to a generator within the disinfection maintenance station 26 for the production of vapour phase hydrogen peroxide (VPHP), and the compartment 12 is charged with VPHP, as indicated by arrows b in FIG. 6. The reduced pressure in the compartment 12 causes the VPHP to permeate through the channels of the endoscope 10.

After charging the compartment 12 for a pre-determined length of time, the compartment 12 is again connected to the suction device within the station 26 to remove VPHP from the compartment 12 and from the channels of the endoscope 10, as indicated by arrows a in FIG. 5. The compartment 12 is then connected to a dry sterile nitrogen gas vessel within the station 26, and the compartment is charged with dry sterile nitrogen gas, as indicated by arrows b in FIG. 6.

Once the above cycle is complete, the endoscope 10 remains stored within the sealed compartment 12 until required in a surgical procedure. This storage may be carried out with the tray 11 remaining docked on the station 26, and either under a charge of dry sterile nitrogen gas, as shown in FIG. 6, or under reduced pressure, as shown in FIG. 5. Alternatively, these two options may be combined, or periodically alternated between. A further alternative is to withdraw the tray 11 from the station 26, but with the compartment 12 remaining sealed, as shown in FIG. 4, and retaining the sterile nitrogen gas charge and/or the reduced pressure therein.

The invention claimed is:

1. A method for maintaining disinfection of medical equipment following processing thereof, comprising placing disinfected equipment in a sealed chamber comprising
   a reusable tray having a rigid construction, and having a downwardly-dished, inner compartment defined by a generally planar base and surrounding walls upstanding therefrom; and
   a protective cover comprising a rigid lid having tapered edges engaging with complementary tapered edges provided on the walls of the tray, thereby to provide a substantially gas-tight seal;
   wherein at least one of said tray and said cover has a valve for connection to a disinfection maintenance station comprising a suction device and a vessel for a disinfectant;
   and wherein the tray is housed within an oxygen-impermeable pouch, also having a valve for connection to said disinfection maintenance station, and arranged to communicate with said valve in at least one of said tray and said cover, and subsequently performing the following steps:
   (A) reducing pressure within the sealed chamber using said suction device, thereby to cause evaporation of residual moisture;
   (B) removing atmospheric oxygen from the sealed chamber, thus further reducing pressure within the sealed chamber, using a gas scavenger present in at least one sachet;
   (C) charging the sealed chamber with a disinfectant from said vessel, said disinfectant being selected from a disinfectant gas and a disinfectant vapour;
   and subsequently maintaining a biostatic environment within the sealed chamber, whereby viable inter-procedural disinfected storage time for said medical equipment is greater than 3 hours.

2. The method as claimed in claim 1, wherein maintenance of a biostatic environment within the sealed chamber is achieved by maintaining reduced pressure.

3. The method as claimed in claim 1, wherein maintenance of a biostatic environment within the sealed chamber is achieved by maintaining the charge of disinfectant from step (C).

4. The method as claimed in claim 1, wherein evaporated residual moisture from step (A) and atmospheric water vapour are removed from the sealed chamber using a desiccant.

5. The method as claimed in claim 1, wherein in step (B) at least one further gas selected from carbon dioxide, hydrogen sulphide, sulphur dioxide, hydrogen chloride and ammonia is removed from the sealed chamber using at least one appropriate further gas scavenger, wherein said at least one further gas scavenger includes a material selected from finely divided iron powder and activated carbon.

6. The method as claimed in claim 1, wherein the sealed chamber is provided with an oxygen indicator, to provide a visual indication of the condition of the chamber.

7. The method as claimed in claim 1, wherein the disinfectant comprises at least one component selected from dry disinfectant nitrogen gas and hydrogen peroxide vapour.

8. The method as claimed in claim 1, wherein the re-usable tray is further provided with a single-use, disposable tray-liner formed of a flexibly deformable, sheet material such that in use the tray-liner is able to conform itself substantially to the contours of the tray.

9. The method as claimed in claim 1, wherein said at least one gas scavenger sachet is activated by removing a tear-off strip to expose said scavenger to atmospheric oxygen.

10. The method as claimed in claim 1, wherein multiple sealed chambers individually housed in pouches are provided within a rack to enable disinfection of a plurality of articles of medical equipment to be maintained simultaneously, and independently of one another, and wherein removal of a selected article of medical equipment from its sealed chamber does not compromise disinfection of other articles of medical equipment also housed in like chambers within the rack.

11. The method as claimed in claim 10, wherein said rack comprises a plurality of disinfection maintenance stations, each comprising a port for engaging with the valve of a said pouch housing a said sealed chamber, each said port enabling fluid connection of a said sealed chamber to a said suction device for performance of step (A).

12. The method as claimed in claim 11, wherein each said port further enables fluid connection of a said sealed chamber to a said vessel for disinfectant, for performance of step (C).

* * * * *